United States Patent
Cuschieri et al.

(10) Patent No.: US 6,705,989 B2
(45) Date of Patent: Mar. 16, 2004

(54) RETRACTOR FOR USE IN ENDOSCOPIC SURGERY AND MEDICAL INSTRUMENT FOR INTRODUCING A RETRACTOR AND METHOD FOR THE USE OF A RETRACTOR IN ENDOSCOPIC SURGERY

(75) Inventors: Alfred Cuschieri, Fife (GB); Timothy Graham Frank, Fife (GB)

(73) Assignee: Karl Storz GmbH & Co. KG (DE)

(*) Notice: Subject to any disclaimer, the term of this patent is extended or adjusted under 35 U.S.C. 154(b) by 145 days.

(21) Appl. No.: 09/991,837

(22) Filed: Nov. 6, 2001

(65) Prior Publication Data

US 2002/0111536 A1 Aug. 15, 2002

Related U.S. Application Data

(63) Continuation of application No. PCT/EP00/03604, filed on Apr. 20, 2000.

(30) Foreign Application Priority Data

May 6, 1999 (DE) .......................... 199 20 869

(51) Int. Cl.$^7$ .............................. A61B 17/02
(52) U.S. Cl. ......................... 600/208; 600/216
(58) Field of Search ........................ 600/206, 208, 600/210, 213, 216, 229; 604/161

(56) References Cited

U.S. PATENT DOCUMENTS

| 3,630,198 | A | * | 12/1971 | Henkin | |
|---|---|---|---|---|---|
| 4,354,491 | A | * | 10/1982 | Marbry | |
| 5,307,805 | A | | 5/1994 | Byrne | 606/198 |
| 5,382,231 | A | | 1/1995 | Shlain | 128/898 |
| 5,450,842 | A | * | 9/1995 | Tovey et al. | 600/206 |
| 5,522,788 | A | | 6/1996 | Kuzmak | 600/141 |
| 5,558,665 | A | | 9/1996 | Kieturakis | 606/1 |
| 5,607,446 | A | * | 3/1997 | Beehler et al. | 606/198 |
| 5,624,381 | A | | 4/1997 | Kieturakis | 600/206 |
| 5,662,676 | A | * | 9/1997 | Koninckx | 606/198 |
| 5,741,284 | A | * | 4/1998 | Karlsson | 604/160 |
| 5,787,897 | A | | 8/1998 | Kieturakis | 128/898 |
| 5,860,987 | A | | 1/1999 | Ratcliff et al. | 606/113 |
| 5,871,496 | A | | 2/1999 | Ginn et al. | 606/190 |
| 5,904,649 | A | * | 5/1999 | Andrese | 600/204 |

FOREIGN PATENT DOCUMENTS

| DE | 43 18 951 | 12/1994 |
|---|---|---|
| DE | 693 10 345 | 6/1997 |
| WO | WO 93/13713 | 7/1993 |
| WO | WO 93/22973 | 11/1993 |
| WO | WO 97/23158 | 7/1997 |

* cited by examiner

Primary Examiner—Cary E. O'Connor
(74) Attorney, Agent, or Firm—St. Onge Steward Johnston & Reens LLC

(57) ABSTRACT

The invention relates to a retractor for use in endoscopic surgery, comprising a shaft having a hand piece arranged on the proximal end thereof and whose distal end can be moved out of an initially extended and straight position, whereby the adjustable distal end consists of several link elements that can be moved into a ring-shaped structure and the ring-shaped structure can be bent in relation to the shaft. In order to produce a retractor which can be used atraumatically and can be handled in a highly hygienic manner, it is also proposed in accordance with this invention that the distal end of the shaft should be moved into the closed ring structure and the closed ring structure be bent in a continuous manner at an angle of up to 90 degrees. The invention also relates to a medical instrument for introducing a retractor into a human or animal body and to a method for the use of a retractor in endoscopic surgery.

15 Claims, 4 Drawing Sheets

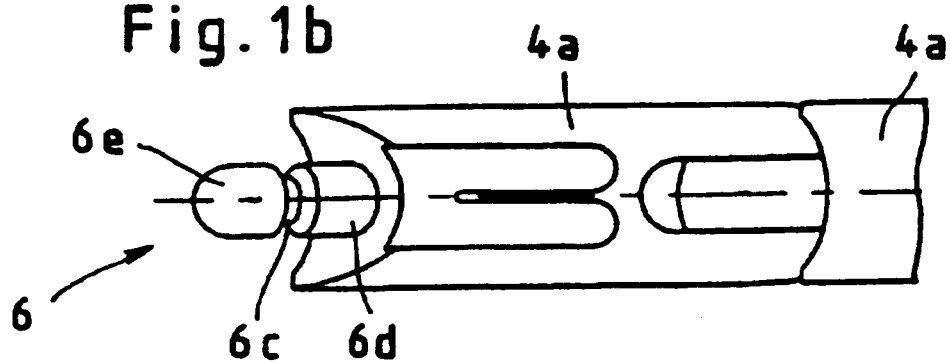
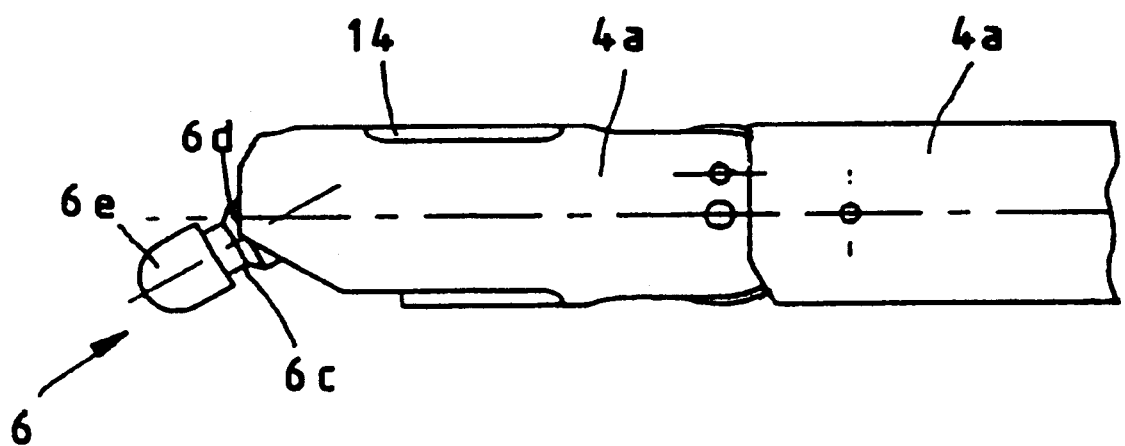

RETRACTOR FOR USE IN ENDOSCOPIC SURGERY AND MEDICAL INSTRUMENT FOR INTRODUCING A RETRACTOR AND METHOD FOR THE USE OF A RETRACTOR IN ENDOSCOPIC SURGERY

This application is a continuation of pending International Application PCT/EP00/03604 filed on Apr. 20, 2000, which designates the United States and claims priority from German Application DE19920869.7 filed on May 6, 1999.

FIELD OF THE INVENTION

The invention relates to a retractor for use in endoscopic surgery, comprising a shaft (1) having a hand piece (2) arranged on the proximal end thereof and whose distal end can be moved out of an initially extended and straight position, whereby the adjustable distal end consists of several link elements (4) that can be moved into a ring-shaped structure and said ring-shaped structure can be bent in relation to the shaft (1). The invention also relates to a medical instrument for introducing a retractor into a human or animal body and to a method for the use of a retractor in endoscopic surgery.

BACKGROUND OF THE INVENTION

Retractors are used in endoscopic surgery to remove organs and similar bodily parts, which are not to be treated, from the operating area during an operation using endoscopic viewing. Contrary to the fan-type retractors customarily used, retractors of the type mentioned at the outset have the advantage that, upon re-closing the retractor, scarcely any further danger exists that the bodily parts handled by the retractor will suffer bruising injuries. Such a fan-type retractor is known, for example, from U.S. Pat. No. 5,307,805.

A retractor of the aforementioned type is known for instance from DE 693 10 345 T2. These retractors, in straight, extended position, are introduced into the body, for instance the abdominal area, and once inserted, are displaced by turning the hand piece. Use of the adjustable link elements can lead to bruising of bodily parts to be treated. In addition, the known types of retractors can only be partially cleansed, particularly in the area connecting the shaft and the hand piece.

On the basis of this technological status, the invention is based on the task of creating a retractor that ensures safe, atraumatic use and which in addition can be handled in a highly hygienic manner. In addition, the invention is based on the task of providing a medical instrument for introducing a retractor into human or animal bodies as well as a method for using a retractor in endoscopic surgery.

The invention solves this task in that the distal end of the shaft can be moved into a closed ring structure and that the closed ring structure can be bent continuously to an angle up to 90 degrees to the shaft.

Because, in the retractor of this invention, the retractor can be moved into a closed ring structure, it becomes possible to avoid bruising injuries of the kind that can occur in practice with known retractors. The design of the closed ring structure, in addition, has the advantage that the moved distal end of the shaft is stable and weight bearing in itself. The possibility of also bending the ring structure in relation to the shaft allows for an especially simple and safe use of the retractor of this invention.

In accordance with a first demonstration of the invention, the distal end of the shaft is moved by means of a tool while being viewed in the endoscope. This demonstration of the invention is distinguished by its simple structure, since it dispenses with an independent mechanism for moving the distal end of the retractor shaft.

To facilitate opening and/or closing of the ring structure by means of a tool, recesses are provided in the front most link element, and a tool, such as a pincer in particular, can engage in said recesses in order to move the link element.

In a second execution of the invention, the distal end of the retractor shaft can be moved by means of an interior or exterior Bowden cable.

In accordance with an initial practical demonstration, the locking element is designed as a notch element which can be secured in a notch retainer of the first link element that is connected with the immobile part of the shaft. This firm interlocking makes it possible to apply relatively great pressure through the closed ring structure.

In an alternative version of the invention, the locking element consists of a magnet.

In accordance with a practical demonstration of the invention, the ring structure can be bent at least 90 degrees to the shaft by means of a hinge between the rigid shaft portion and the first link element in both directions from the level of the ring structure.

To facilitate sterilizing the retractor of this invention, it is further proposed that the hand piece and shaft are reversibly connected by means of an adapter piece so that the parts can be individually cleaned.

The shaft and the adapter piece connected to the hand piece may be assembled in an especially simple manner because the adapter piece and shift are joined together by engaged notching.

To secure the shaft to the adapter piece it is proposed that the adapter piece have an axial bore in which a notch element is mounted which can be activated from outside by means of a button for securing the shaft. In order to connect the shaft and hand piece, it is merely necessary to move the proximal free end of the shaft into the axial bore of the adapter piece connected with the hand piece, until the notch element in the adapter piece secures the shaft by notching.

To ensure a firm connection between shaft and adapter piece by means of a notch element of the adapter piece, and also to allow the release of this connection through activation of the button situated on the outside of the adapter piece, the notch element is spring-loaded in the notch position.

Handling the retractor of this invention by the operating team can be facilitated if the weight of the hand piece is determined in such a way that the hand piece serves as a counterweight to the bodily part gripped by the ring structure.

The invention's solution to the task of providing a medical instrument for introducing a retractor into a human or animal body is characterized by a shaft with a basically semicircular profile in cross-section, whose distal end has the shape of a self-cutting tip.

The use of this insertion device, according to the invention, offers an alternative to the use of classical hollow-cylinder trocars. The invention's insertion device, after the retractor is introduced into the body, can be removed again so that the retractor can then be freely moved.

The invention's method for using a retractor in endoscopic surgery is characterized by the following steps:
 a) introducing a retractor shaft in straight, extended position into the body through an artificial bodily opening;
 b) moving the distal end of the shaft into a closed ring structure;

c) bending the displaced distal end of the shaft from the level of the ring structure opposite the shaft d) removal of an internal organ or other tissue from the operating area in order to make room and visibility for the endoscopic intervention; and e) replacing the retractor shaft into the straight, extended position for removal from the body For the introduction of the invention's retractor into the body it is suggested that a medical instrument be used whose shaft has a basically semicircular cross-section and whose distal end has the form of a self-cutting tip. Use of this insertion tool designed according to the invention allows a simple, safe introduction of the retractor and also ensures that this tool can be removed again after the retractor is inserted in order to increase the working space available to the retractor.

BRIEF DESCRIPTION OF THE DRAWINGS

Additional characteristics and advantages of the invention can be seen from the following description of the related illustrations, which depict two demonstration models of a retractor according to the invention and one model of the insertion tool according to the invention. The illustrations are as follows:

FIG. 1b Lateral view of a second demonstration form of the locking element as in FIG. 1a.

FIG. 1c Lateral view of the locking element of FIG. 1b bent at 90 degrees.

DETAILED DESCRIPTION OF THE DRAWINGS

Figure 1A:
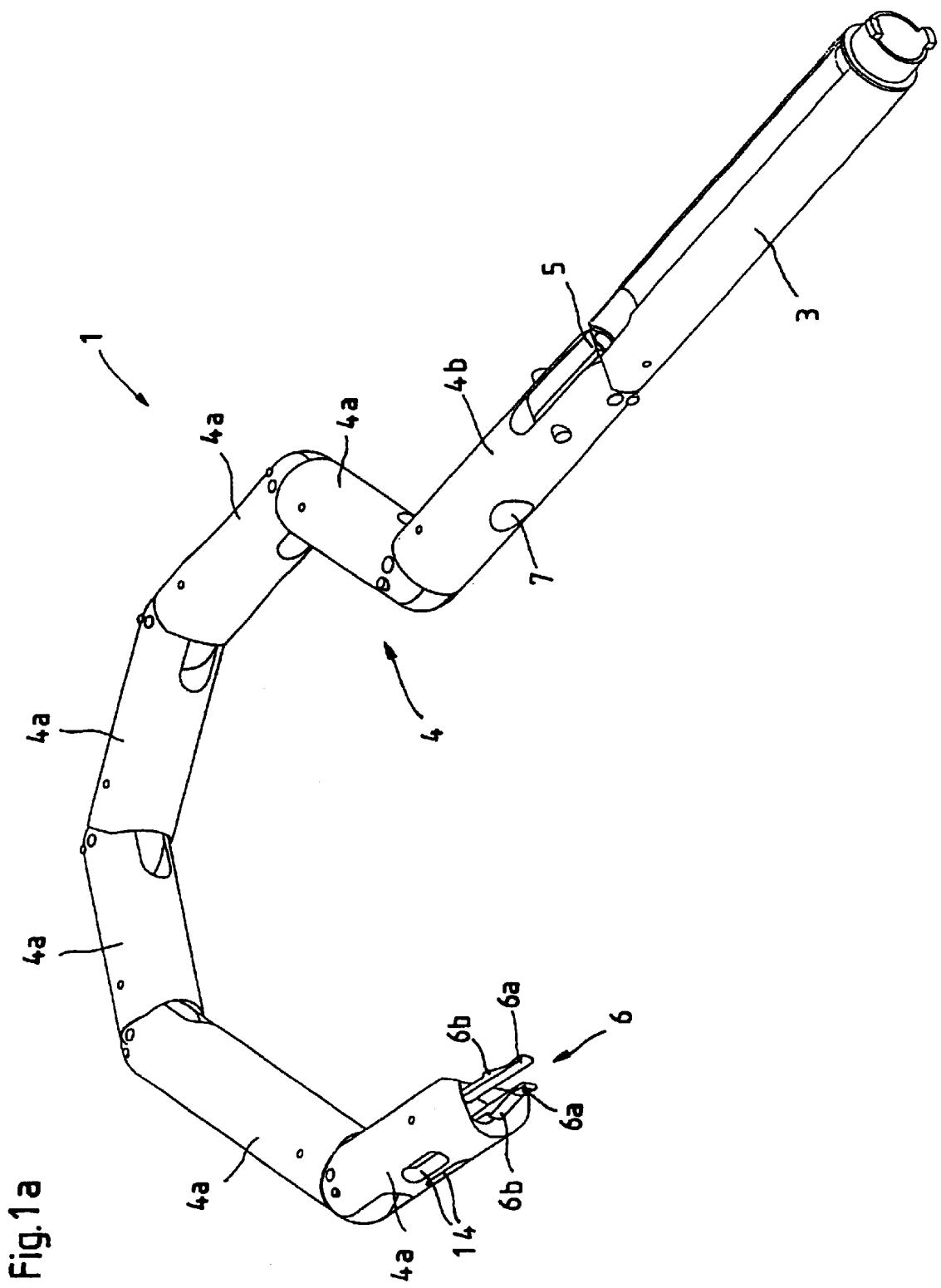
FIG. 1a Perspective view of a retractor according to the invention without hand piece, with partially moved distal end and a locking element in accordance with an initial demonstration.

FIG. 1a shows a shaft 1 of a retractor, but without the yet-to-be-described hand piece 2, which in the retractor's assembled state is attached at the proximal end of the shaft 1.

The illustrated shaft 1 consists of a rigid part 3 that is to be connected to the hand piece 2 and, at the distal end, of seven link elements 4 connected flexibly with the rigid part 3. While the front six link elements 4a from the free distal end of the shaft 1 can be tilted toward one another in the same plane, the link element 4b connected with the rigid part 3 of the shaft 1 can be bent by a hinge 5 from the plane of the link elements 4a continuously up to 90 degrees to the rigid part 3 of the shaft 1.

To form the closed ring structure by means of the link elements 4a, on the front free end of the first link element 4a a notch element 6 is installed, which can be secured in a notch retainer 7 which is joined in the link element 4b connected with the rigid part 3. In the first model, shown in FIG. 1a, the notch element 6 consists of two parallel arms 6a directed away from the free end of the link element 4a, with one notch spring 6b attached to each in order to grip the edge of the notch retainer 7 from behind when the ring structures of the link elements 4a are closed.

In the second model, illustrated in FIGS. 1b and 1c, the locking element to secure the front most link element 4a to the shaft is once again formed as a notch element 6. In this case the notch element 6 is formed of a rod 6d equipped with a surrounding ring groove 6c, which rod is equipped on its free end with a semicircular-shaped head 6e. To form the closed ring structure the notch element 6 is inserted into the notch retainer 7 until a spherical notch (not shown) arranged in the notch retainer 7 and acting in the axial direction is engaged in the surrounding ring groove 6c and thus the front most link element 4a is securely linked with the shaft 1.

Figure 2:
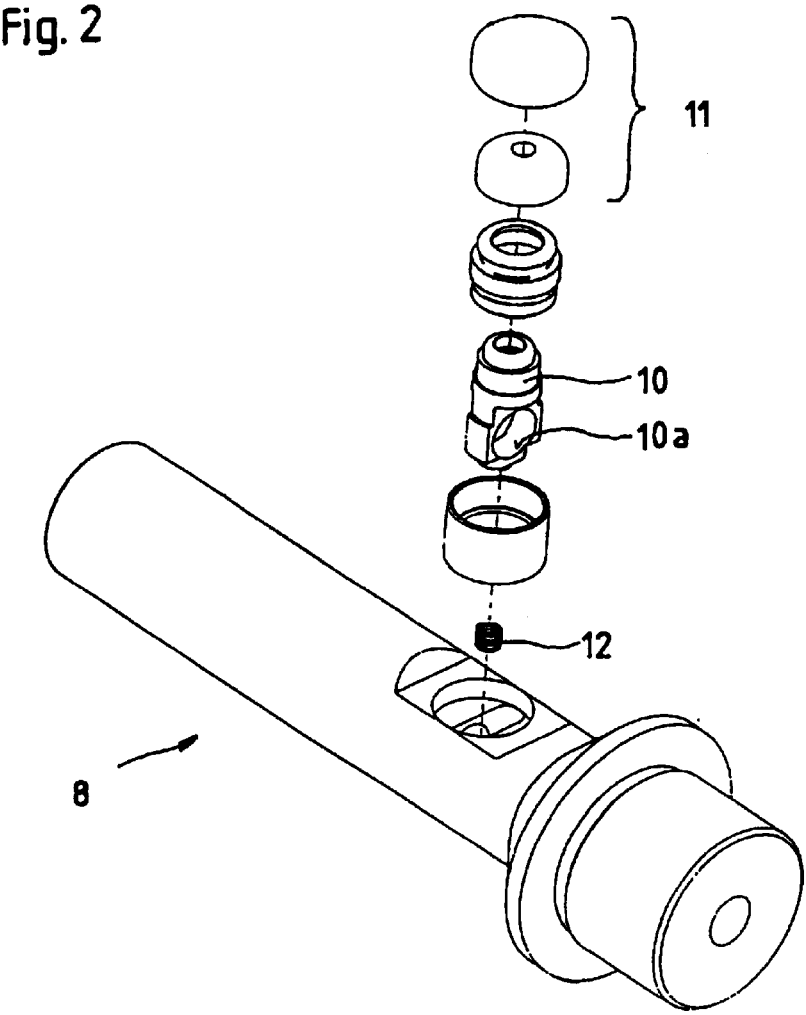
FIG. 2 Perspective drawing of an adapter piece.
Figure 3:
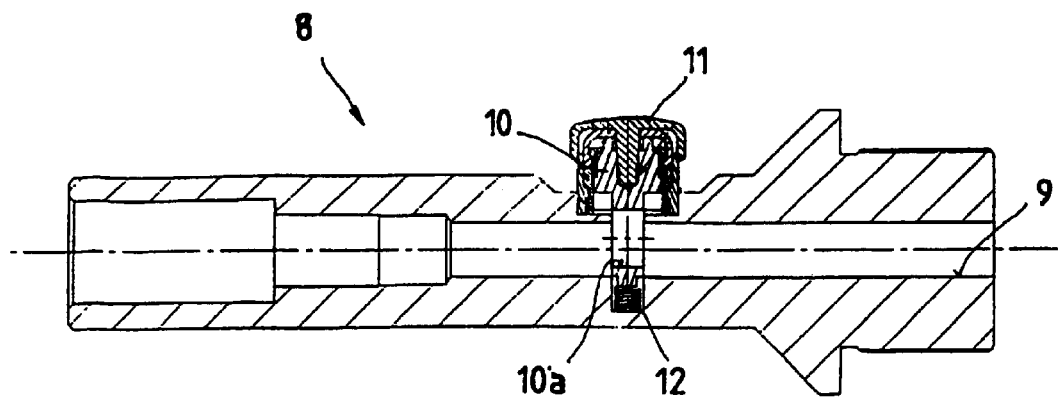
FIG. 3 Longitudinal section through the adapter piece according to FIG. 2 in assembled state.
Figure 4:
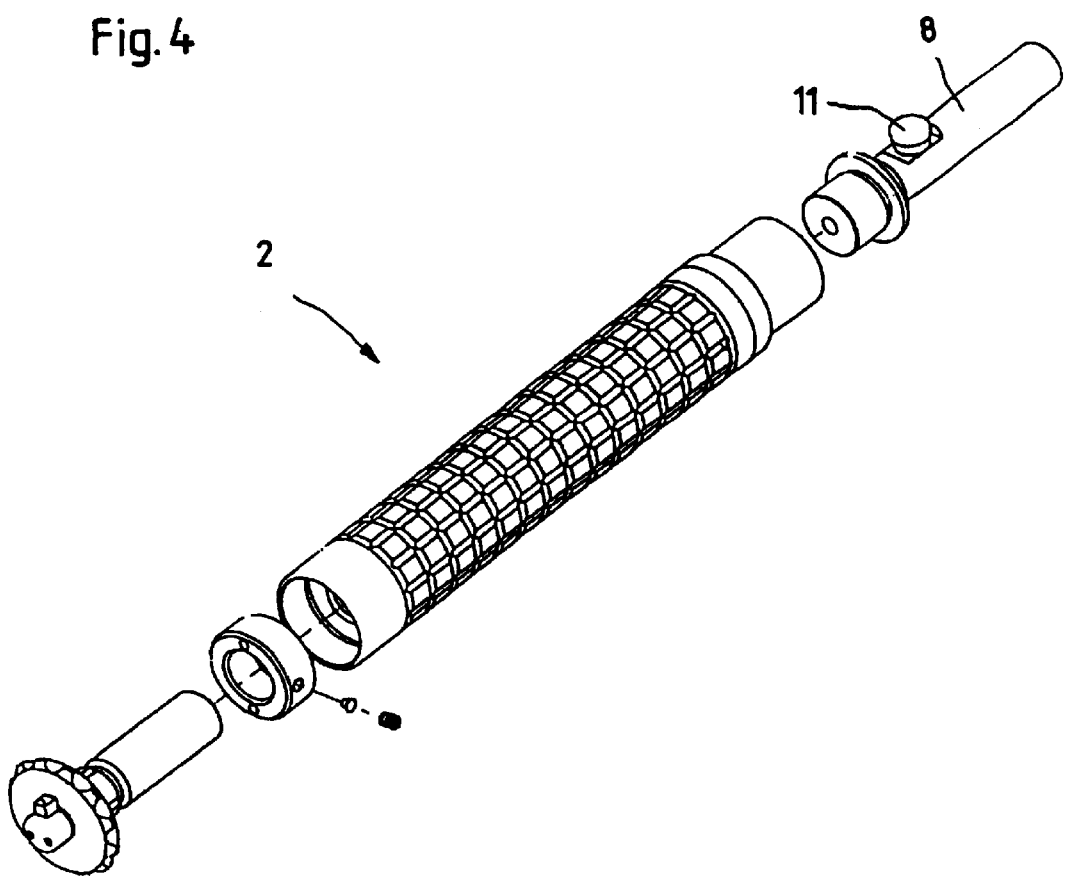
FIG. 4 Perspective drawing of the hand piece and adapter piece.

The hand piece 2 shown in FIG. 4 is connected by an adapter piece 8 according to FIG. 2 and FIG. 3 with the proximal end of the shaft 1. While the adapter piece 8 as a rule is firmly connected with the hand piece 2, for instance through gluing, the connection between the adapter piece 8 and the rigid part 3 of the shaft 1 is designed as a reversible notch connection so that the shaft 1 can be separated simply and quickly from the hand piece 2 or the adapter piece 8 for purposes of cleaning.

As can be seen from FIGS. 2 and 3, the adapter piece 8 has an axial through-bore 9, in which an externally activated notch element 10 is installed. To secure the shaft 1, the notch element 10 has a recessed bore 10a. The lock is activated from outside the adapter piece by means of a button 11 by which the notch element 10 can be pressed in against the force of a power spring 12 into the adapter piece 8 until the recessed bore 10a moves flush with the through-bore 9 so that the shaft 1 can be inserted into the adapter piece 8 or withdrawn from it.

In addition to the illustrated link between the shaft 1 on the one hand and hand piece 2 or adapter piece 8 on the other hand by way of the described notch element 10, all other separable connections can of course be used for connecting these components in order to provide a retractor that is simple to use and to clean.

Figure 5:
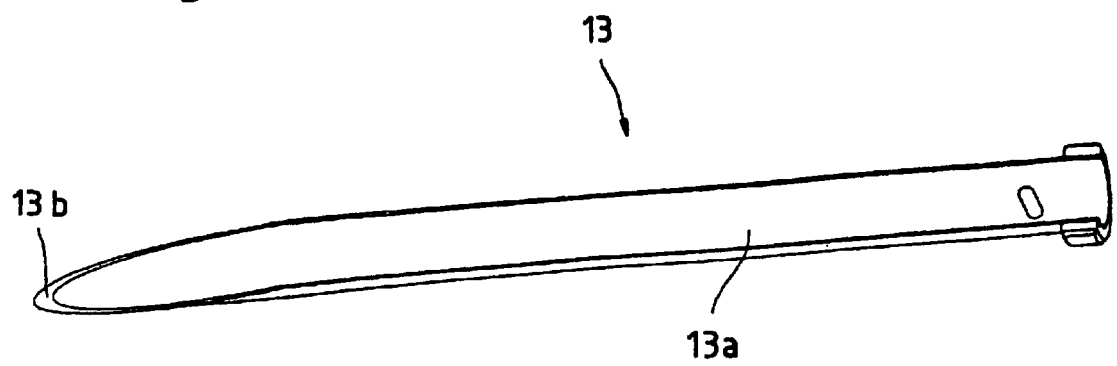
FIG. 5 Perspective view of an insertion tool in accordance with the invention.

FIG. 5 shows, finally, an insertion device 13 to introduce a retractor into a human or animal body. The insertion device 13 has a shaft 13a that is basically semicircular in cross-section, whose distal end is designed as a self-cutting tip 13b.

Working with the illustrated retractor is described as follows.

To introduce the retractor into the otherwise already prepared operating area, for instance in the abdominal cavity, the insertion device 13 with the self-cutting point 13b in front is forced through the tissue, and then the reactor is introduced into the operating area along the concave inner side of the shaft 13a using endoscope visual control. As soon as the retractor is introduced into the body, the insertion device 13 can be withdrawn again so that the refractor is freely movable.

In the starting position in which the retractor is introduced into the body, the retractor is extended straight, that is, all link elements 4 are directed flush with the rigid part 3 of the shaft 1. In order to be able to remove organs or similar bodily parts from the operating area, it is necessary, after introducing the retractor, to arrange its distal end in such a way that it securely grips and holds the said bodily parts. For this purpose, the link elements 4a in the illustrated model are turned so far toward one another by means of a tool, for instance a securing pincer, using endoscopic visual control, until they form a closed ring structure and the notch element 6 engages in the notch retainer 7. To facilitate moving the link elements 4a by means of the tool, the front most link element 4a, bearing the locking element, has recesses 14 into which the tool can engage for opening or closing the ring structure. With this closed ring structure it is possible, practically without any danger of injury, to keep the corresponding bodily parts safely away from the operating area in order to make space and visibility for the endoscope intervention.

In order to make this type of retractor design even more useful, the ring structure, in addition, can be bent over the hinge 5 continuously up to 90 degrees to the plane of the ring structure.

The weight of the hand piece 2 is to be measured in such a way that the hand piece serves as a counterweight to the bodily part gripped by means of the ring structure. This makes it unnecessary to press forcefully on the hand piece, as is necessary with traditional retractors.

To remove the retractor from the body the link elements 4 are moved, with visual control by endoscope, back into the straight extended starting position by means of a tool, so that the retractor can once again be withdrawn from the body without difficulty.

After release of the notch connection between shaft 1 and hand piece 2 or adapter piece 8, the shaft 1 can then be sterilized independently of the hand piece 2.

In addition to the illustrated model of a retractor whereby the distal end of the shaft 1 is moved by means of a tool with control by endoscopic viewing, in an alternative model the distal end of the shaft 1 is moved by means of a Bowden cable. This Bowden cable is then secured, instead of on the notch element 6, on the front free end of the front most link element 4a and is led to hand piece 2 through the bore 7 (notch recess) in the shaft 1. In the extended position the Bowden cable then runs between bore 7 and the free end of the front most link element 4a in a groove. For the extension of the retractor a Bowden cable is drawn correspondingly in a groove on the exterior of the ring.

Along with the hygienic considerations of this retractor that can be cleaned simply and well, it is distinguished by the fact that it ensures safe, atraumatic use.

| Key | |
|---|---|
| 1 | Shaft |
| 2 | Hand piece |
| 3 | Rigid part |
| 4 | Link element |
| 4a | Link element |
| 4b | Link element |
| 5 | Hinge |
| 6 | Notch element |
| 6a | Arm |
| 6b | Notch spring |
| 6c | Ring groove |
| 6d | Rod |
| 6e | Head |
| 7 | Notch retainer |
| 8 | Adapter piece |
| 9 | Passage bore |
| 10 | Notch element |
| 10a | Recess bore |
| 11 | Button |
| 12 | Pressure spring |
| 13 | Insertion device |
| 13a | Shaft |
| 13b | Point |
| 14 | Recess |

What is claimed is:

1. Retractor for use in endoscopic surgery with a shaft at whose proximal end a hand piece is mounted and whose distal end can be moved out of an initially extended, straight position, whereby the adjustable distal end consists of several link elements that can bend toward one another and can be moved into a ring-shaped structure, and whereby this ring-shaped structure can be bent in relation to a rigid part of the shaft, characterized in that the distal end of the shaft can be moved into a closed ring structure, whereby at the forward free end of the front most link element a locking element is situated, with which the front most link element can be secured for forming the closed ring structure, and in that the closed ring structure can be bent continuously at an angle up to 90 degrees to the rigid part of the shaft.

2. Retractor in accordance with claim 1, characterized in that the distal end of the shaft can be moved, while viewed in the endoscope, into the closed ring structure by means of a tool.

3. Retractor in accordance with claim 2, characterized in that on the closest link element there are recesses into which a tool, in particular a pincer, can engage to move the link elements.

4. Retractor in accordance with claim 1, characterized in that the distal end of the shaft can be moved into the closed ring structure by means of a Bowden cable.

5. Retractor in accordance with claim 4, characterized in that the locking element is designed as a notch element, which can be secured in a notch retainer of the first link element that is connected with the rigid part of the shaft.

6. Retractor in accordance with claim 4, characterized in that the locking element is in the form of a magnet.

7. Retractor in accordance with claim 1, characterized in that the ring structure can be bent at least 90 degrees to the rigid part of the shaft in both directions from the plane of the ring structure by means of a hinge between the rigid part of the shaft and the first link element.

8. Retractor in accordance with claim 1, characterized in that the hand piece and the shaft are connected reversibly by way of an adapter piece.

9. Retractor in accordance with claim 8, characterized in that the shaft is interlocking with the adapter piece.

10. Retractor in accordance with claim 8, characterized in that the adapter piece has an axial bore in which a notch element that is activated from outside by means of a button is mounted for securing the shaft.

11. Retractor in accordance with claim 10, characterized in that the notch element is spring-loaded in the notch position.

12. Retractor in accordance with claim 1, characterized in that the hand piece is formed as a counterweight to the ring structure.

13. Retractor in accordance with claim 1, further comprising an insertion tool having a shaft with a profile that is basically semicircular in cross-section, whose distal end has the form of a self-cutting tip.

14. Method for the use of a retractor, in accordance with claim 1, in endoscopic surgery, characterized by the following steps:

a) introducing a retractor shaft in straight, extended position into the body through an artificial bodily opening;

b) moving the distal end of the shaft into a closed ring structure;

c) bending the displaced distal end of the shaft from the plane of the ring structure opposite the shaft;

d) removal of an internal organ or other tissue from the operating area in order to make room and visibility for the endoscopic intervention; and e) replacing the retractor shaft into the straight, extended position for removal from the body.

15. Method in accordance with claim 14, characterized in that, to introduce the retractor shaft into the body, a medical instrument is used whose shaft has a basically semicircular profile in cross-section and whose distal end has the form of a self-cutting tip.

* * * * *